(12) United States Patent
Garnavi et al.

(10) Patent No.: US 10,657,838 B2
(45) Date of Patent: *May 19, 2020

(54) SYSTEM AND METHOD TO TEACH AND EVALUATE IMAGE GRADING PERFORMANCE USING PRIOR LEARNED EXPERT KNOWLEDGE BASE

(71) Applicant: International Business Machines Corporation, Armonk, NY (US)

(72) Inventors: Rahil Garnavi, Macleod (AU); Dwarikanath Mahapatra, Travancore (AU); Pallab K. Roy, Kingsville (AU); Ruwan B. Tennakoon, Hawthorn (AU)

(73) Assignee: International Business Machines Corporation, Armonk, NY (US)

( * ) Notice: Subject to any disclaimer, the term of this patent is extended or adjusted under 35 U.S.C. 154(b) by 358 days.

This patent is subject to a terminal disclaimer.

(21) Appl. No.: 15/459,457

(22) Filed: Mar. 15, 2017

(65) Prior Publication Data

US 2018/0268733 A1   Sep. 20, 2018

(51) Int. Cl.
*G09B 19/00* (2006.01)
*G06N 3/04* (2006.01)
(Continued)

(52) U.S. Cl.
CPC ............ *G09B 19/00* (2013.01); *G06F 3/167* (2013.01); *G06F 19/321* (2013.01);
(Continued)

(58) Field of Classification Search
CPC ........ G09F 3/013; G06F 3/005; G09B 19/003
See application file for complete search history.

(56) References Cited

U.S. PATENT DOCUMENTS 6,991,464 B2   1/2006   Liebert
7,052,277 B2   5/2006   Kellman
(Continued)

OTHER PUBLICATIONS

The University of Sydney, "Virtual Ophthalmology Clinic", http://sydney.edu.au/medicine/eye/virto/web2-singlecase/, Accessed on Feb. 1, 2017, 1 page.

(Continued)

*Primary Examiner* — Xuan M Thai
*Assistant Examiner* — Sadaruz Zaman
(74) *Attorney, Agent, or Firm* — Scully, Scott, Murphy & Presser, P.C.; Joseph Petrokaitis

(57) ABSTRACT

A learning sub-system models search patterns of multiple experts in analyzing an image using a recurrent neural network (RNN) architecture, creates a knowledge base that models expert knowledge. A teaching sub-system teaches the search pattern captured by the RNN model and presents to a learning user the information for analyzing an image. The teaching sub-system determines the teaching image sequence based on a difficulty level identified using image features, audio cues, expert confidence and time taken by experts. An evaluation sub-system measures the learning user's performance in terms of search strategy that is evaluated against the RNN model and provides feedback on overall sequence followed by the learning user and time spent by the learning user on each region in the image.

15 Claims, 10 Drawing Sheets

(51) Int. Cl.

| | |
|---|---|
| *G06K 9/62* | (2006.01) |
| *G06F 3/16* | (2006.01) |
| *G06F 19/00* | (2018.01) |
| *G06K 9/00* | (2006.01) |
| *G09B 7/06* | (2006.01) |
| *G09B 23/28* | (2006.01) |
| *G16H 50/70* | (2018.01) |
| *G16H 50/20* | (2018.01) |
| *G06N 3/08* | (2006.01) |
| *G16H 50/50* | (2018.01) |
| *G16H 30/40* | (2018.01) |
| *G09B 5/06* | (2006.01) |
| *G10L 15/26* | (2006.01) |
| *G10L 15/18* | (2013.01) |

(52) U.S. Cl.
CPC ....... *G06K 9/00604* (2013.01); *G06K 9/6254* (2013.01); *G06K 9/6262* (2013.01); *G06K 9/6273* (2013.01); *G06N 3/0427* (2013.01); *G06N 3/0445* (2013.01); *G06N 3/0454* (2013.01); *G06N 3/084* (2013.01); *G09B 7/06* (2013.01); *G09B 23/286* (2013.01); *G16H 30/40* (2018.01); *G16H 50/20* (2018.01); *G16H 50/50* (2018.01); *G16H 50/70* (2018.01); *G06K 2209/05* (2013.01); *G09B 5/06* (2013.01); *G10L 15/18* (2013.01); *G10L 15/265* (2013.01)

(56) References Cited

U.S. PATENT DOCUMENTS

| | | | | |
|---|---|---|---|---|
| 8,811,657 | B2* | 8/2014 | Teiwes | A61B 3/113 128/922 |
| 9,039,419 | B2 | 5/2015 | Dietrich et al. | |
| 9,179,184 | B1* | 11/2015 | Skolicki | H04N 21/442 |
| 9,423,870 | B2 | 8/2016 | Teller et al. | |
| 9,823,744 | B2* | 11/2017 | Publicover | G06F 21/64 |
| 10,002,311 | B1* | 6/2018 | Garnavi | G06K 9/00604 |
| 2002/0047828 | A1* | 4/2002 | Stern | A61B 3/028 345/156 |
| 2011/0270123 | A1* | 11/2011 | Reiner | A61B 3/113 600/558 |
| 2012/0113209 | A1* | 5/2012 | Ritchey | H04N 5/2254 348/14.02 |
| 2013/0012789 | A1* | 1/2013 | Horseman | A61B 5/6887 600/301 |
| 2013/0057573 | A1* | 3/2013 | Chakravarthula | G06F 3/005 345/619 |
| 2013/0063550 | A1* | 3/2013 | Ritchey | G16H 40/63 348/36 |
| 2013/0137076 | A1 | 5/2013 | Perez et al. | |
| 2015/0009118 | A1 | 1/2015 | Thomas et al. | |
| 2015/0338915 | A1* | 11/2015 | Publicover | G06K 9/0061 345/633 |
| 2017/0061286 | A1* | 3/2017 | Kumar | G06Q 30/00 |
| 2017/0068119 | A1* | 3/2017 | Antaki | H04N 5/2251 |
| 2017/0075419 | A1* | 3/2017 | Parthasarathy | G09B 19/003 |
| 2017/0123492 | A1* | 5/2017 | Marggraff | G06F 3/0236 |
| 2018/0098908 | A1* | 4/2018 | Chien | A61H 5/00 |

OTHER PUBLICATIONS

Succar, T., et al., "The impact of the Virtual Ophthalmology Clinic on medical students' learning: a randomised controlled trial", Eye (2013), Jul. 2013, pp. 1151-1157, vol. 27.

Khanna, A., "EyeSim—Medical Traning for Opthalmology", EON Reality Inc., http://www.eonreality.com/portfolio-tems/eyesim/, Accessed on Feb. 1, 2017, 6 pages.

Gribova, V.V., et al., "Computer teaching simulator with virtual reality for ophthalmology", The 9th International Conference on Information Technology and Applications (ICITA 2014), Jul. 2014, 3 pages.

Weller, J.M., et al., "Simulation in clinical teaching and learning", Medical Journal of Australia, May 2012, p. 594, vol. 196, No. 9.

Nodine, C.F., et al., "How Experience and Training Influence Mammography Expertise", Academic Radiology, Oct. 1999, pp. 575-585, vol. 6, No. 10.

Speelman, C., et al., "Skill Acquisition in Skin Cancer Detection", Perceptual and Motor Skills, 2010, pp. 277-297, vol. 110, No. 1.

Sherbino, J., et al., "The Relationship Between Response Time and Diagnostic Accuracy", Academic Medicine, Jun. 2012, pp. 785-791, vol. 87, No. 6.

Krasne, S., et al., "Applying perceptual and adaptive learning techniques for teaching introductory histopathology", Journal of Pathology Informatics, Dec. 2013, 8 pages, vol. 4, No. 34.

Zou, X, et al., "Learning-Based Visual Saliency Model for Detecting Diabetic Macular Edema in Retinal Image", Computational Intelligence and Neuroscience, Hindawai Publishing Corporation, Dec. 2015, 10 pages, vol. 2016, Article ID 7496735.

Helbren, E., et al., Towards a framework for analysis of eye-tracking studies in the three dimensional environment: a study of visual search by experienced readers of endoluminal CT colonography, The British Journal of Radiology, Feb. 2014, 6 pages, vol. 87, No. 1037.

Krupinski, E., et al., "Eye Tracking Helps Improve Accuracy in Radiology", BioPhotonics, Jun. 2006, https://www.photonics.com/Article.aspx?AID=43855, Accessed on Feb. 1, 2017, 9 pages.

Mallett, S., et al., "Tracking Eye Gaze during Interpretation of Endoluminal Three-dimensional CT Colonography: Visual Perception of Experienced and Inexperienced Readers", Radiology, Dec. 2014, pp. 783-792, vol. 273, No. 3.

Meining, A., et al., ""Eye-tracking" for assessment of image perception in gastrointestinal endoscopy with narrow-band imaging compared with white-light endoscopy", Endoscopy 2010, Jun. 2010, pp. 652-655, vol. 42.

Dennies, E., et al., "Investigating the Use of Eye-Tracking Technology for Assessment—A case study of research and innovation at Nether Hall Special School", Full Research Report, Dec. 2015, 39 pages.

Malcolm, G.L., "Combining top-down processes to guide eye movements during real-world scene search", Journal of Vision (2010), Feb. 2010, pp. 1-11, vol. 10(2):4.

Okekoya, O., et al., "An Eye Tracking Interface for Image Search", Proceedings of the 2006 symposium on Eye tracking research & applications (ETRA '06), Mar. 2006, 1 page.

Seiple, W., et al., "Eye-Movement Training for Reading in Patients with Age-Related Macular Degeneration", Investigative Ophthalmology & Visual Science, Aug. 2005, pp. 2886-2896, vol. 46, No. 8.

Perry, L., "UCLA study shows eye-tracking technology improves nursing training", UCLA Newsroom, Aug. 15, 2016, http://newsroom.ucla.edu/releases/ucla-study-shows-eye-tracking-technology-improves-nursing-training, Accessed on Feb. 1, 2017, 3 pages.

Van Den Bogert, N., "On teachers' visual perception and interpretation of classroom events using eye tracking and collaborative tagging methodologies", Technische Universiteit Eindhoven, Jan. 2016, 130 pages.

Cooper, S., et al., "Can eye-tracking technology improve situational awareness and student feedback during simulation?", Final Report 2014, http://emergencyeyetracking.com/wp-content/uploads/2013/12/SD12-2432_Monash_Cooper_Final-Report.pdf, Accessed on Feb. 1, 2017, 39 pages.

John, B., et al., "Collaborative Eye Tracking for Image Analysis", ETRA 2014, Mar. 2014, pp. 239-242.

Ciotti, G., "7 Marketing Lessons from Eye-Tracking Studies", Kissemtrics Blog, https://blog.kissmetrics.com/eye-tracking-studies/, Accessed on Feb. 1, 2016, 16 pages.

Sensomotoric Instruments (SMI), "Case Study: Eye Tracking & Teachers' Classroom Perception", http://www.smivision.com/en/gaze-and-eye-tracking-systems/applications/psychology-psychiatry-psycholinguistics/teachers-classroom-perception.html, Accessed on Feb. 6, 2017, 2 pages.

Tobii Pro, "Educational Research", http://www.tobiipro.com/fields-of-use/education/educational-research/, Accessed on Feb. 1, 2017, 3 pages.

(56) References Cited

OTHER PUBLICATIONS

Dhein, C.R., et al., "Teaching the Didactic Aspects of Opthalmology and Dermatology Using an off-Site Instructor", Journal of Veterinary Medical Education, Feb. 2005, pp. 57-67, vol. 32, No. 1.
Kuchenbecker, J., et al., "Internet-based teaching and learning in opthalmology", Opthalmologe, Oct. 2001, 6 pages, vol. 98, No. 10, with English Language abstract.
List of IBM Patents or Patent Applications Treated as Related, dated Nov. 16, 2017, 2 pages.

\* cited by examiner

SYSTEM AND METHOD TO TEACH AND EVALUATE IMAGE GRADING PERFORMANCE USING PRIOR LEARNED EXPERT KNOWLEDGE BASE

FIELD

The present application relates generally to computers and computer applications, and more particularly to image analysis and learning systems.

BACKGROUND

Image analysis and interpretation contribute to many medical (e.g., detecting diseased tissues), surveillance (e.g., forest fire detection), and industrial applications (e.g., detecting manufacturing defects). All application scenarios require that the human observer have minimum level of proficiency in analyzing the relevant images. It is observed that requisite experience increases proficiency in image analysis. The knowledge responsible for this improvement is gathered through practice and interaction with other domain experts. However, access to experts is limited to very few persons of a field due to factors such as remoteness, or lack of an established local program in the relevant field. This limits the ability of an inexperienced person to learn the necessary knowledge, which in turn can have serious consequences in some fields such as medical pathology detection, forest fire detection or identifying drought/flood risks from satellite images.

Existing virtual reality systems and simulated systems that provide teaching may be limited to cases that are part of the training data set diagnosed by an expert, and may not be able to cope with new images that present unseen scenarios, features, and/or characteristics. Those systems also do not exploit image features as part of a teaching process.

BRIEF SUMMARY

An image analysis teaching and evaluation system and method may be provided. The system, in one aspect, may include a hardware processor executing a user interface, the hardware processor retrieving an image from a database of images and presenting the image on the user interface displayed on a display device. An eye tracker may be coupled to at least a camera and coupled to the hardware processor, the eye tracker monitoring eye movements of a learning user analyzing the image and generating a sequence of eye movements. The user interface may receive annotations on the image input by the learning user. A microphone may be coupled to the hardware processor. The hardware processor may receive via the microphone audio data associated with the image spoken by the learning user, the hardware processor translating the audio data into text, the hardware processor extracting keywords from the text. The hardware processor may correlate the sequence of eye movements, the annotations and the keywords according to their time of occurrence. The hardware processor may extract image features from the image and map the image features with the sequence of eye movements, the annotations and the keywords that are correlated. The hardware processor may generate a search pattern of the learning user based on the image features mapped with the sequence of eye movements, the annotations and the keywords that are correlated. A knowledgebase may be stored in a storage device, and may include a recurrent neural network model that predicts a likelihood of an expert image analyzer focusing on a feature in the image. The knowledgebase may also include an expert image analyzer's search pattern of the image with associated audio cues and time spent by the expert image analyzer on the feature. The hardware processor may generate the expert's search pattern of the image by executing the recurrent neural network model, and display the expert's search pattern on the user interface while playing associated audio cues retrieved from the knowledgebase. The hardware processor may further zoom in the feature predicted by the recurrent neural network model on the user interface.

A method of teaching image analysis and evaluating analysis results, in one aspect, may include retrieving an image from a database of images and presenting the image on the user interface displayed on a display device. The method may also include transmitting a signal to an eye tracker comprising at least a camera coupled to the hardware processor, the signal representing a notification to the eye tracker to monitor eye movements of a learning user analyzing the image and generating a sequence of eye movements based on the eye tracker monitoring the eye movements. The method may also include receiving via the user interface, annotations on the image input by the learning user. The method may further include receiving via a microphone coupled to the hardware processor, audio data associated with the image spoken by the learning user, and translating the audio data into text and extracting keywords from the text. The method may also include correlating the sequence of eye movements, the annotations and the keywords according to their time of occurrence. The method may further include extracting image features from the image and mapping the image features with the sequence of eye movements, the annotations and the keywords that are correlated. The method may also include generating a search pattern of the learning user based on the image features mapped with the sequence of eye movements, the annotations and the keywords that are correlated. The method may also include retrieving from a knowledgebase stored in a storage device, a recurrent neural network model that predicts a likelihood of an expert image analyzer focusing on a feature in the image and time spent by the expert image analyzer on the feature. The method may also include generating an expert's search pattern of the image by executing the recurrent neural network model, and displaying the expert's search pattern on the user interface while playing associated audio cues retrieved from the knowledgebase, and further zooming in the feature predicted by the recurrent neural network model on the user interface.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
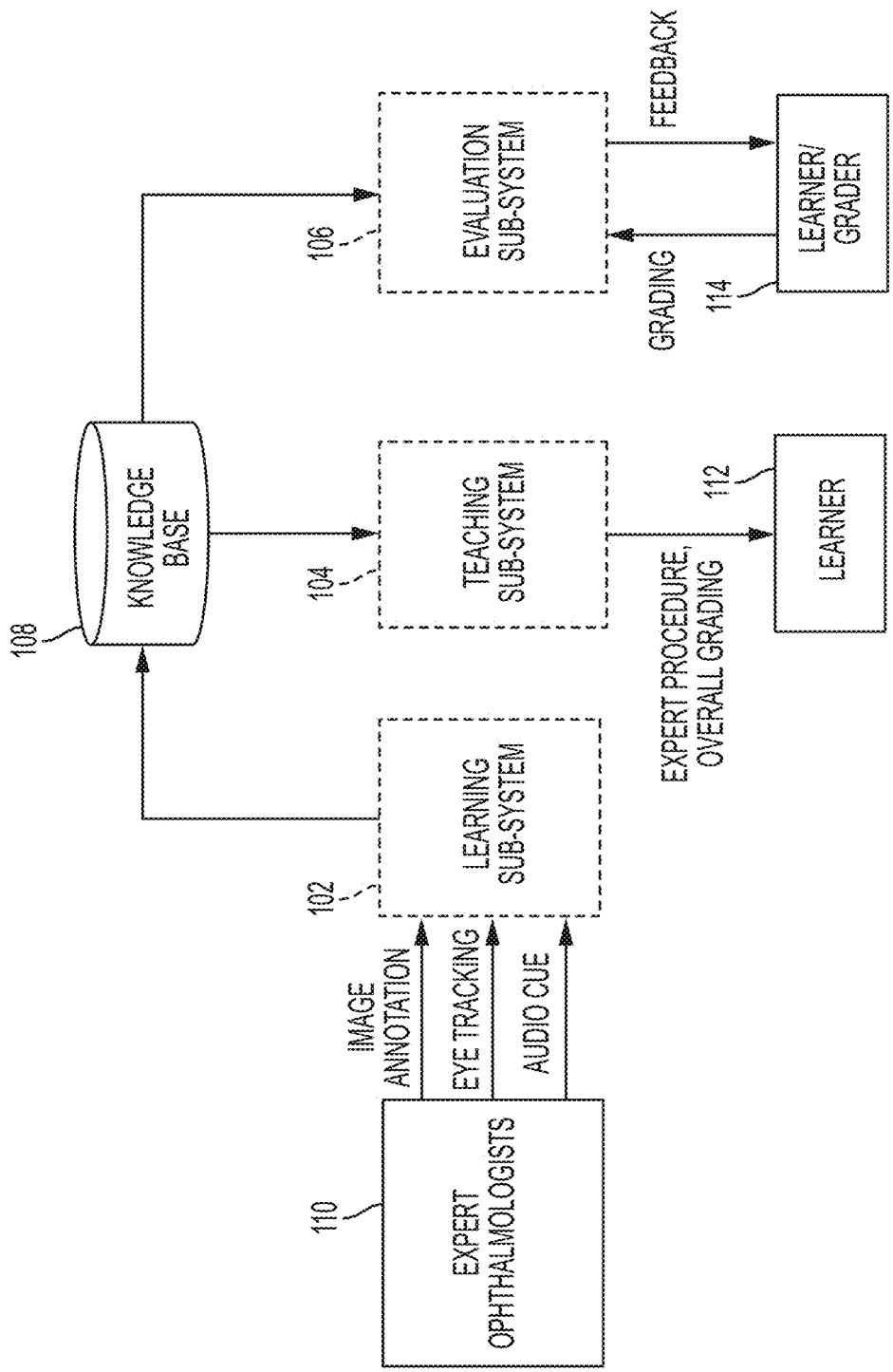
FIG. 1 is a diagram illustrating an overview of components in one embodiment of the present disclosure.

A system and method are presented that automatically teach less experienced graders how to better interpret and analyze images to achieve the desired objective. The system in one embodiment uses an enriched knowledge base created from annotations provided by domain experts, and leverages this learned knowledge to guide learners how to effectively analyze images. The system in one embodiment includes a facility to correct learners' mistakes, provide feedback on their performance and output a score quantifying their performance. An example if provided below with reference to retinal images as a use case. However, the system can be used for any application that involves image analysis and interpretation.

Diagnosis and management of retinal conditions such as diabetic retinopathy (DR) or Age related macular Degeneration (AMD) is important as they are one of the leading causes of blindness in the world. With the increasing number of such patients around the world, clinicians who are adequately trained to detect incidence of DR and AMD, and recommend appropriate action are needed. Training ophthalmologists is a resource intensive procedure that requires considerable time and effort from experienced ophthalmologists and clinicians.

The system and method of the present disclosure in one embodiment may provide an automatic training module (e.g., for ophthalmologists in this use case example) that performs the following functions: 1) Assists operators in learning to identify the relevant patterns necessary to detect retinal pathologies without direct supervision of experts; 2) Suggests locations of interest (pathologies) to the less experienced grader using automatic algorithms to ensure consistency; 3) Provides feedback on the operators' proficiency and identify areas where further training is required, by comparing their detections with the detections of an automatic algorithm. The system in one embodiment outputs consistent results in order to reduce bias due to subjectivity.

The system in one embodiment may be used to teach image analysts (e.g., inexperienced ophthalmologists) how to grade images associated with different retinal pathologies (such as DR, AMD or glaucoma). In one embodiment, the teaching is based on a knowledge base that is created from the input of expert ophthalmologists prior to the teaching stage. The system in one embodiment guides the learners and/or students through the different stages followed by experts to analyze a retinal image. During the teaching phase, the system provides insight into the thinking process of experts and other information that helps them make an accurate evaluation. After the teaching phase, the system in one embodiment presents an evaluation phase where the skills learned by the learner are put to test and the learner receives feedback on performance and ways to improve knowledge and performance.

The system in one embodiment allows a user to interactively learn from expert knowledge. Reliable feedback may be provided to eliminate the need for long apprenticeship of new graders. Facility to learn new patterns and/or insight from new images may be provided in a systematic fashion, for instance, rather than subjective experience. The system allows for improving fluency of grading so that optimal time is spent on grading new cases. An automatic training module is provided that may minimize subjectivity of feedback.

The system and methods in one embodiment of the present disclosure provide an automated teaching of learners, e.g., a novice clinician or student to analyze retinal images for identifying incidence of pathologies. In one embodiment, the system includes a teaching module and an evaluation system. The teaching module presents the knowledge captured by the learning module to a trainee. The teaching module may highlight which regions in fundus images give greater information about presence of DR, the importance of different landmarks and how to address difficult cases. The evaluation system may assess the response of the user and evaluate the response for accuracy and provide feedback on any mistakes, accurate identifications and provide a performance score.

The system may use previously learnt expert knowledge on retinal image analysis for training less experienced ophthalmologists. Detailed step by step analysis may be provided to the learner of the thinking process of experts and the most important considerations for pathology identification. The system may quantify the performance of the grader and provide accurate feedback on areas of improvement.

The system and method of the present disclosure may provide following advantages over the existing perceptual training systems, for example, that teach medical image analysis. The use of eye tracking information and audio cues in combination with learner image features facilitate the learner to grasp additional information that would not be available with image only perceptual learning systems. The creation of a knowledge base (or oracle) enables the teaching module to present the information considered to be important to the learner for grading DR. The knowledge base also allows for generalizing or applying the expert knowledge to previously unseen images. The evaluation module can be used as a reference against which a novice grader can evaluate his or her findings.

Figure 6A:
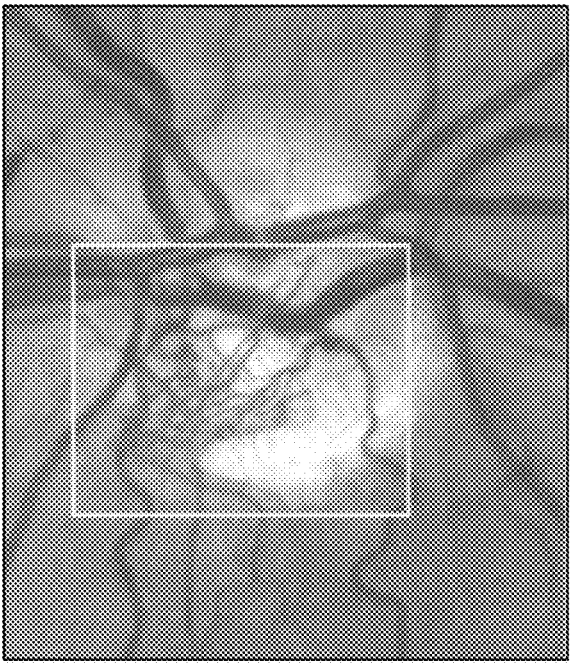
FIGS. 6A and 6B shows an example UI display by a teaching system showing an image for analysis in one embodiment of the present disclosure.
Figure 6B:
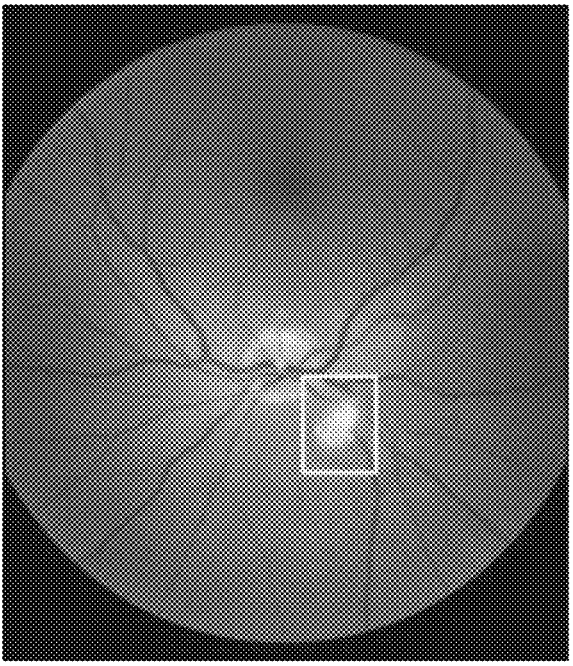

FIG. 1 is a diagram illustrating an overview of components in one embodiment of the present disclosure. The components shown may include one or more hardware processors that execute the shown modules or sub-systems. A learning module (also referred to as a learning sub-system or system) 102 may learn and create a knowledge base 108 by monitoring a domain expert 110 analyzing an image, for example, by monitoring the expert's image annotation, eye tracking and audio cue while the domain expert 110 is analyzing the image. FIGS. 6A and 6B illustrate example screenshot displays of a learning module in operation for constructing the knowledge base (e.g., 108 in FIG. 1). The UI example shown in FIGS. 6A and 6B may be presented with an image on the user interface screen, for example, for allowing an expert user to enter annotations on the image. In addition, as described above, an eye tracker system monitors the expert user's eye pattern the while expert user is analyzing the image.

Co-pending U.S. patent application Ser. No. 15/429,735, entitled "Generating an Enriched Knowledge Base from Annotated Images" and filed on Feb. 10, 2017, discloses a system to learn and create a knowledge base from expert annotations. That application is incorporated herein by reference in its entirety. The knowledge base described in that co-pending U.S. patent application is created from information sources of experts including their eye tracking data, audio cues and annotations made on images.

The learning module 102 generates a model of search patterns (eye-gaze patterns while analyzing an image) of multiple experts in analyzing an image using a recurrent neural network (RNN) architecture. The learning module 102 creates a knowledge base (oracle) 108 that models expert knowledge with which the system of the present disclosure may generalize or identify new unseen scenarios. The learning module 102 may use audio cues, time taken to analyze a particular region of the image, intra expert variability and image features (learned using expert annotations) to categorize the difficulty of a particular test image.

The learning module 102 may receive audio cues from an expert stating whether a region is a clear pathology region or difficult pathology region, and use the audio cues in learning. The learning module 102 may present experts with images from a database and request the experts to grade the DR severity. The experts' eye movements and audio are recorded. Once the severity is identified, the learning module 102 may request the experts to highlight (or otherwise annotate) pathologies that led to the conclusions. The learning module 102 uses image annotations to extract image features (pixel level image features), and uses the image features, audio and eye tracking to model the image analysis sequence.

The learning module 102 learns landmarks that are important in diagnosing the relevant disease and their relative order of importance in images, how to distinguish between normal and diseased cases, and also what extra information and/or features to look for when examining a challenging case, and relevant features for pathology analysis. In one embodiment, the knowledge base 108 has the following information modules: 1) A set of learned convolutional filters (also referred to as dictionaries) that can distinguish between the following cases: a) clearly identifiable normal regions; clearly identifiable pathological regions; b) normal regions that were not easily identifiable; c) pathology regions that were not easily identifiable; 2) Eye tracking data depicting the analysis sequence followed by the expert and time spent examining each region; and 3) A set of keywords and assertions used by the experts in describing the grading process.

A teaching module (also referred to as a teaching sub-system or system) 104 may present an image to a user (e.g., a learner or student) 112, and provides a fixed time (e.g., a period of time) during which the user is allowed to analyze or examine the image. The teaching module 104 may record the user's (e.g., student's) eye movement, and also guide the user through the expert analysis sequence while presenting the user with audio cues on a graphical user interface. The teaching module 104 may provide feedback on the sequence followed by user, allow the user 112 to explore individual pathologies, and allow the user to explore similar and complementary cases.

The teaching module 104 teaches a search strategy captured by a recurrent neural network (RNN) model, presents the user with the information on which pathology contributes more towards the overall diagnosis, and determines the teaching image sequence based on a difficulty level identified using: image features, audio cues, expert confidence and time taken by experts.

The evaluation module (also referred to as an evaluation sub-system or system) 106 measures the user's performance in terms of the user's search strategy that is recorded and evaluated against the expert's search strategy. The evaluation module 106 provides a feedback on overall sequence followed by the user 114 and the time spent on each region. The combination of the three sub-systems 102, 104 and 106, creates a system capable of training and supporting users for image analysis, for example, ophthalmologist in remote locations. In one embodiment, component of the teaching sub-system 104 and the evaluation sub-system 106 may overlap.

Figure 2:
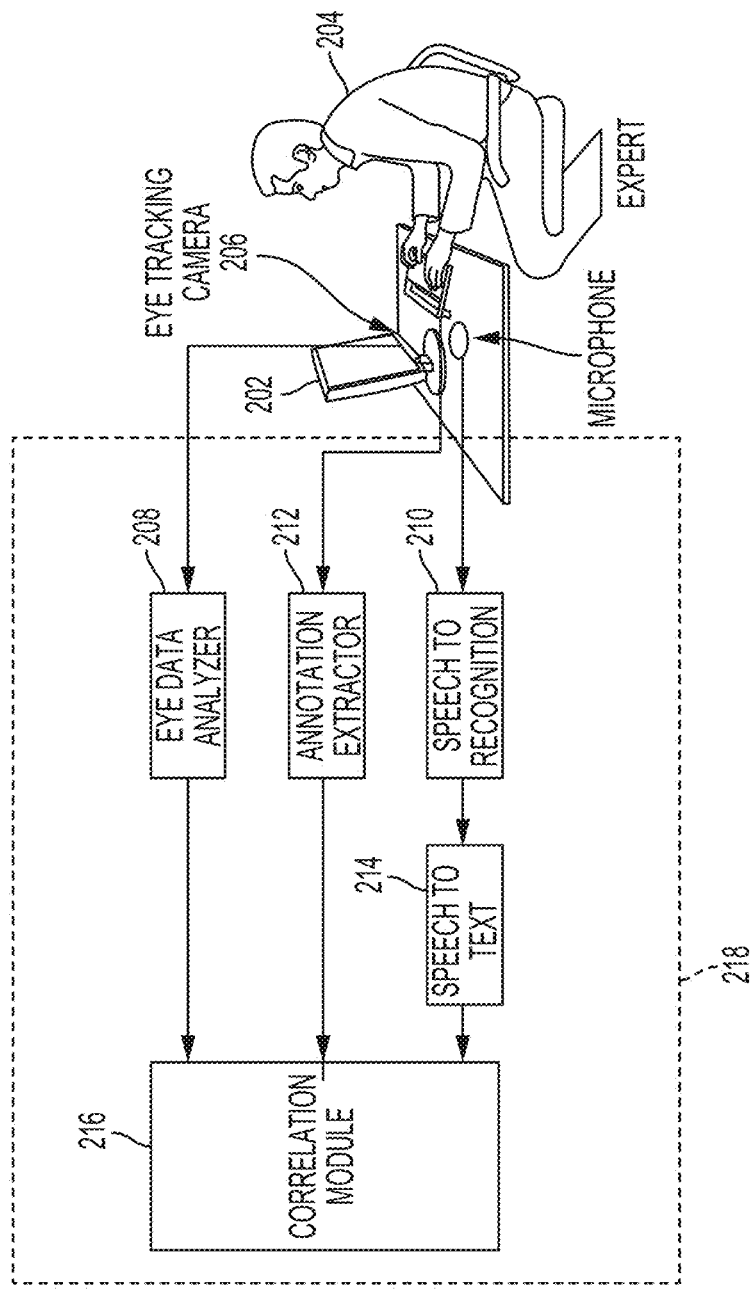
FIG. 2 illustrates high level system components in one embodiment of the present disclosure that constructs a learning system's knowledge base.

FIG. 2 illustrates high level system components in one embodiment of the present disclosure that constructs a learning system's knowledge base. At least one hardware processor 218 executes the components shown in FIG. 2, for example, a user interface program or software, an eye data analyzer 208, annotation extractor 212, speech recognition 210, speech to text conversion 214 and correlation 216. An eye tracker such as an eye tracking camera 206 is coupled to the hardware processor An image initially stored into the knowledge base is presented through a user interface (UI) 202 on a visual display device, via to an expert or like user 204. An eye-gaze-tracker, e.g., an eye tracking camera 206, or another hardware that includes a lens component and a processor component, is notified that a new image is made available and a reference code is associated with this notification. For example, the system or the UI notifies the eye gaze tracker 206 that the new image is loaded and displayed on the UI. The system creates a reference code, which includes a time stamp indicating the time the image is loaded on a display, and an identification of the image, e.g., the name associated with the image such as the name of the assessor (and/or name of a patient for a medical image). The eye-gaze tracker starts a new recording, creating an eye-gaze pattern detection session identified by the reference code for this image analysis by the expert.

An audio recorder such as a microphone 208 is notified that a new image is made available. This notification includes the associated reference code, for example, the same reference code associated with the notification received at the eye-gaze tracker. The audio recorder starts a new audio recording session for the image identified by the reference code, e.g., responsive to the notification.

The expert 204 by using the visual display on UI 202 enters or draws annotations for the given image. At the same time, the gaze-tracker and the audio recorder capture the expert's visual and audio feedback. The expert 204 interacts with the UI 202 to terminate and store the annotation into the system. The eye-gaze tracker completes the session recording. The audio recorder completes the session recording.

An eye-pattern-extractor 208 extracts the data points of the eye-gaze movements and timecodes them. For example, the eye movement is recorded by an eye-gaze tracker 206 with a specific frequency. An inbuilt software keeps track of which eye gaze instance corresponds to what time stamp (e.g., in terms of hh:mm:ss (hour, minute, second) extracted from the computer's CPU clock or the like). Based on the time stamp, the system of the present disclosure may synchronize the eye gaze instances with other input sources such as audio and image annotations.

A speech-recognition component 210 analyzes the audio data in the audio recorder session recording, and detects and timecodes key words that have been spoken by the expert. For example, the audio recorder is constantly recording data and synchronizing the recorded data with the time from the CPU clock. Thus, keywords spoken at specific instances have a time stamp that is synchronous with the eye gaze tracker's data, for example, eye gaze instance. As shown at 214, speech is converted to text including the timecoded key words.

An annotation extractor 212 analyzes the annotations that the expert 204 has made on the image. For example, the annotation drawn by the expert 204 by using the visual display on UI 202 and the image presented to the expert are read by the image annotation extractor 212. The annotation extractor then crops the region within the marked annotations from the image and sends it to the correlation module 216 together with the annotation coordinated and label. For example, if the expert annotated a rectangle (top-left-x:15, top-left-y:20, width-256, height-256) on image x1.jpeg, and gave it the label "hemorrhage" at time-10:30:00, the annotation extractor crops the appropriate region of the image and forwards the following massage to the correlation module [time: 10:30:00, image-name: x1.jpeg, image-data: <pixel values within the marked rectangle extracted from the image>, coordinates: (15,20), label: hemorrhage.

A correlation module 216 in one embodiment takes into account the following items: pre-existing knowledge in a knowledge base, which the correlation module uses to guide the mapping of time-coded input to the corresponding features or measurements; annotations and the time the annotations were entered by the expert, which are attached to the image; time-coded eye-gaze patterns extracted by the eye-pattern-extractor (e.g., eye data analyzer 208), time-coded key words spoken by the expert. The correlation module 216 correlates and cross-references this information, and enriches the metadata of the image into the knowledge base, by using as a key the reference code. Based on the time spent, the particular morphological features that the expert analyzes and pays most attention, the system of the present disclosure in one embodiment identifies regions that are interesting (e.g., showing an abnormality). The regions where the expert spends more time present greater ambiguity and are more difficult to identify and need to be given extra attention during learning, teaching and evaluation. Based on the time spent, the system groups these regions as obvious, less ambiguous and more ambiguous. In addition, by analyzing the time spent on specific morphologies, the system can learn characteristics of difficult examples. The reference code is used to ensure that the analysis of data from multiple sources is of an image with the same reference code. The output of this correlation module is a synchronous knowledge base that has correlated the extracted features and/or analysis with the corresponding time stamp to ensure that the metadata derived from each source is of the same image analyzed at the same time or time frame.

Knowledge Base Creation/Learning Module

The learning module, for example, the correlation module 216 captures knowledge on image analysis by a user (e.g., an expert user) and models the captured knowledge as a learning model to train other users to analyze the image. For example, the learning module captures knowledge on DR diagnosis and severity estimation from expert ophthalmologists and models it such that it can be used in effective training of new ophthalmologists and/or graders. The learning module presents fundus images to the expert ophthalmologists through an interface as shown in FIG. 2, and uses the following features as its input in building the knowledge base: image features, eye tracking data and audio cues.

At the completion of the learning phase, the system of the present disclosure in one embodiment will have generated the following representations: A set of learned dictionaries and/or convolutional filters that can distinguish between the following cases: clearly identifiable normal regions, clearly identifiable pathological regions, normal regions that were not easily identifiable, pathology regions that were not easily identifiable; eye tracking data depicting the analysis sequence followed by the expert, time spent examining each region; and a set of keywords and assertions used by the expert in describing the grading process.

Image Annotations

In one embodiment, the system of the present disclosure presents images to a user, for example, fundus images to an expert ophthalmologist case by case via a user interface 202. The user interface 202 allows the user to annotate the image, for example, by marking the image with an input device. The user, for example, expert ophthalmologists would then annotate regions on the image which shows signs of DR pathologies (such as micro-aneurysms, hemorrhages, neovascularization's) and provide a DR severity score. The learning module accumulates this information and analyzes a collection of such annotations, learning a model representation that best discriminates between regions of DR and non-DR. In one embodiment, the learning module may employ a deep learning architecture to model the image information which is parameterized by a set of learned convolutional filters. In one embodiment, classification approach using convolutional neural networks (CNNs) may be implemented for identifying microaneurysms (MAs). For example, the CNN architecture takes as input the image patches and the labels (for example, described above) that have been annotated by the expert, and based on the input, trains a deep neural network. The deep neural network has cropped image patches (pixel values within the annotated region) as the input and learns to predict a label similar to the label given by the expert as the ground-truth. The neural network can have multiple layers of convolution, max pooling, and activation, based on the architecture that gives the best performance. The updating of weights is done by back propagation of the error between the ground-truth label and the predicted labels. This model learning approach is different from the previous approaches that use hand engineered features to differentiate between DR and non-DR images. The learnt convolutional filters are used in teaching the user about highly discriminative patterns between DR and non-DR pathology, in one embodiment. The learnt convolutional features and/or maps can be applied to new images and the regions that cause these features to be activated to help a user to visualize which regions are important for a particular task (e.g., disease detection). The filters and/or convolution kernels that generate these visualizations can be used on new images to identify the regions that are most interesting.

Eye Tracking Data

As an example, when an expert ophthalmologist is presented with a fundus image, the expert uses his or her experience to direct his or her attention to specific regions on the image and analyzes those specific regions in detail to derive the correct conclusion. The system of the present disclosure is constructed such that it can capture this information and utilize it for training new ophthalmologists. During the learning phase, the system uses an eye-tracker to record the eye movement pattern of the expert. The eye-tracker records where the expert first looks at, and the subsequent regions he or she focuses attention. Human eye movement patterns can be either fixations or saccades. Fixations refer to those instances where the eye is focused on one particular location (and its immediate local neighborhood). Saccades refer to the transition movement of the eye from one location to another. The speed of the eye movement is higher during saccades than during fixations. Reliable algorithms exist to differentiate between fixations and saccades and can be used to identify fixated regions.

The system in one embodiment analyzes the eye fixation information for those regions annotated as having DR pathology by the expert. The system identifies the time spent, the particular morphological features that the ophthalmologist pays most attention and particularly extra attention given to specific areas. The time spent on an area will identify those which are easily identifiable as DR from those which present greater ambiguity. The second category of annotations that present greater ambiguity are the ones that are more difficult to identify and need to be given extra attention during learning, teaching and evaluation. Based on the time spent, the system of the present disclosure groups these regions as obvious, less ambiguous and more ambiguous. In addition, by analyzing the time spent on specific morphologies, the system can learn characteristics of difficult examples. A threshold time may be set or configured for determining whether an image is ambiguous or clearly identifiable. Typical threshold times may be in the range of 2-5 minutes. For example, if the expert spent more than 5 minutes looking at an image region, image characteristics in that region may be considered ambiguous. For example, while creating the knowledge base the expert is also providing the labels/disease class of that region, for example, via annotations and/or audio recording. The system in one embodiment clusters or groups each region based on the label provided by the expert. The system then calculates the time spent on each label by analyzing the time stamps of the eye-gaze recordings. The time value may function as an indicator of how much time an expert spends on different areas of varying severity. If more than one session's data (e.g., multiple experts' sessions, multiple sessions of the same expert) is used in learning, the average time spent on each label from multiple sessions may be computed and used as an indicator of how much time an expert spends on different areas of varying severity.

An eye tracking system or eye tracker may include a head mounted display and/or a web camera. The eye tracking system records the eye movement patterns of the expert as the expert analyzes the presented image and outputs the following information: temporal sequence of fixated regions, for example, in the data format comprising (time stamp, region identifier (ID)); and the time the expert spent in analyzing each region. Time spent in each region is determined by the eye fixation patterns. For example, inbuilt software in modern eye trackers can determine which instance is a fixation (i.e., the observer is closely examining the region), and which instance is a saccade (observer's eye is just passing over that region). When a number of fixations are concentrated on a region then the start and end time of that period is determined and the total spent is calculated. The time spent in analyzing each region may be determined by analyzing the temporal sequence of fixated regions. In one embodiment, the region ID is defined with respect to a normalized coordinate system that is consistent across fundus images from different patients.

A learning system of the present disclosure in one embodiment uses this information to model the expert search strategy for separate disease types and to predict the difficulty or importance of an image region in diagnosing a particular decease type. For example, the expert search strategy is modeled using recurrent neural networks. The eye tracking patterns can also be used to identify onset of fatigue in the expert. For example, when the expert starts to get tired his eye fixation is not steady and his eye gaze movement is beyond the normal acceptable range for normal gazing. For example, when an expert is experiencing fatigue then the recorded data may not be accurate, which may result in generating an accurate model. Therefore, the period of time during which an expert's gaze is associated with fatigue, may be discounted or not used as part of eye-gaze data in generating the knowledgebase or learning model.

Figure 4:
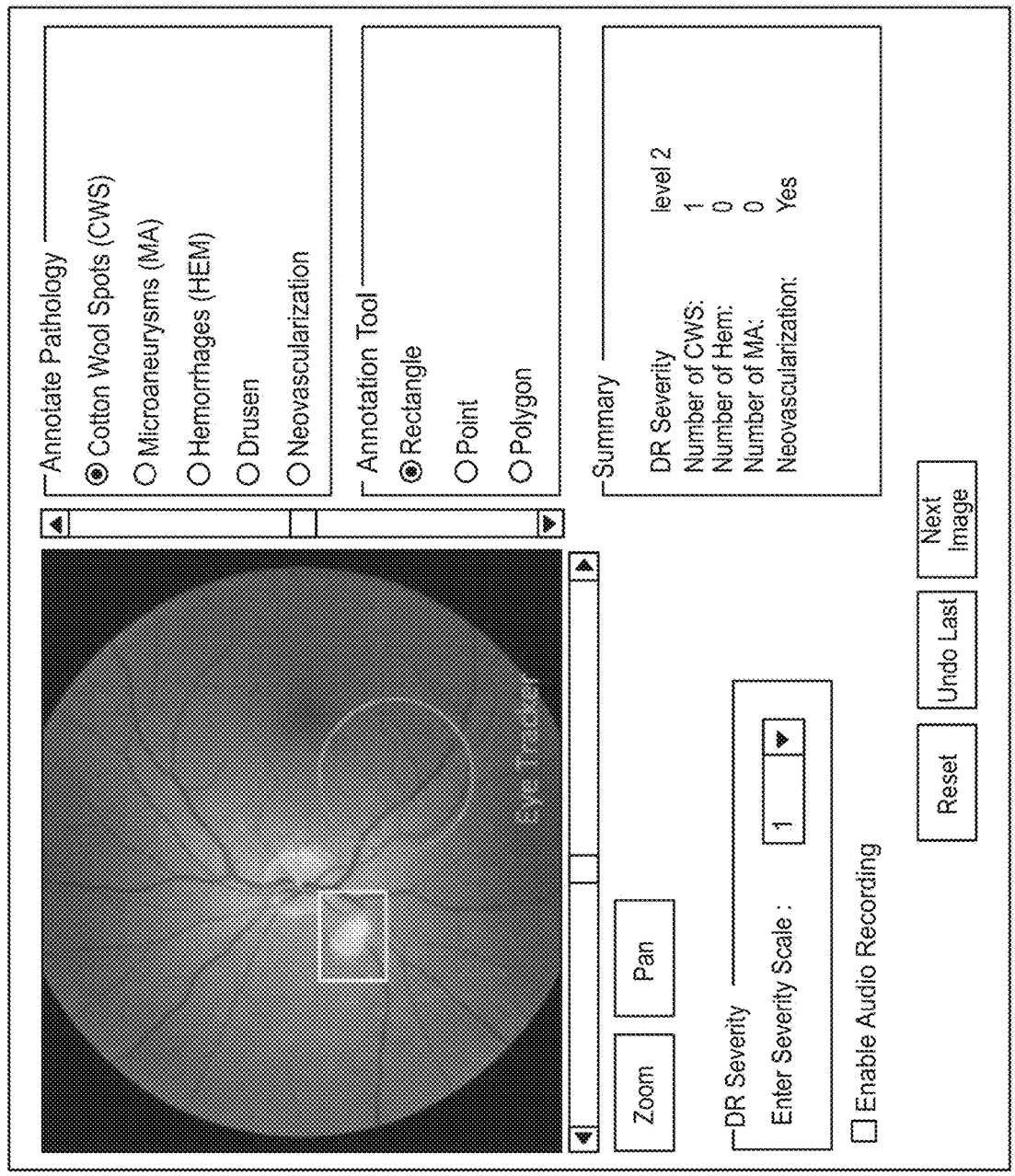
FIG. 4 illustrates a screenshot of a learning module in operation in one embodiment of the present disclosure.

FIG. 4 illustrates a screenshot of a learning module in operation in one embodiment of the present disclosure. A user or an expert (e.g., as shown in FIG. 2) may be presented with an image on the user interface screen and allowed to enter annotations on the image. In addition, as described above, an eye tracker system monitors the user's eye pattern while the user is analyzing the image.

Audio Cues

The system of the present disclosure as shown in FIG. 2 may record any audio input provided by the expert, translate it to text and extract keywords that represent concepts and/or assertions from text. For instance, the output of the speech to text converter is processed by natural language processing algorithms to extract keywords. These keywords are recorded in the database in synchronization with the time stamp of the eye tracking data in order to identify the eye tracking instance to the corresponding audio input. For instance, the time of the audio recording, for example, the time the speech associated with an extracted keyword is uttered, is saved or stored as the corresponding time stamp of that keyword.

A user, for example, an expert ophthalmologist may also provide audio cues while annotating the images. Audio cues may include, but not limited to, information such as 1) regions that present difficulty and/or ambiguity in grading and why; 2) what kind of features and/or knowledge helped the ophthalmologist in resolving that ambiguity; 3) what to look out for in similar cases. A speech to text method converts the speech to text and extracts meaningful concepts from them. For example, a natural language processing algorithm may be utilized to extract keywords from the converted speech-to-text.

Figure 3:
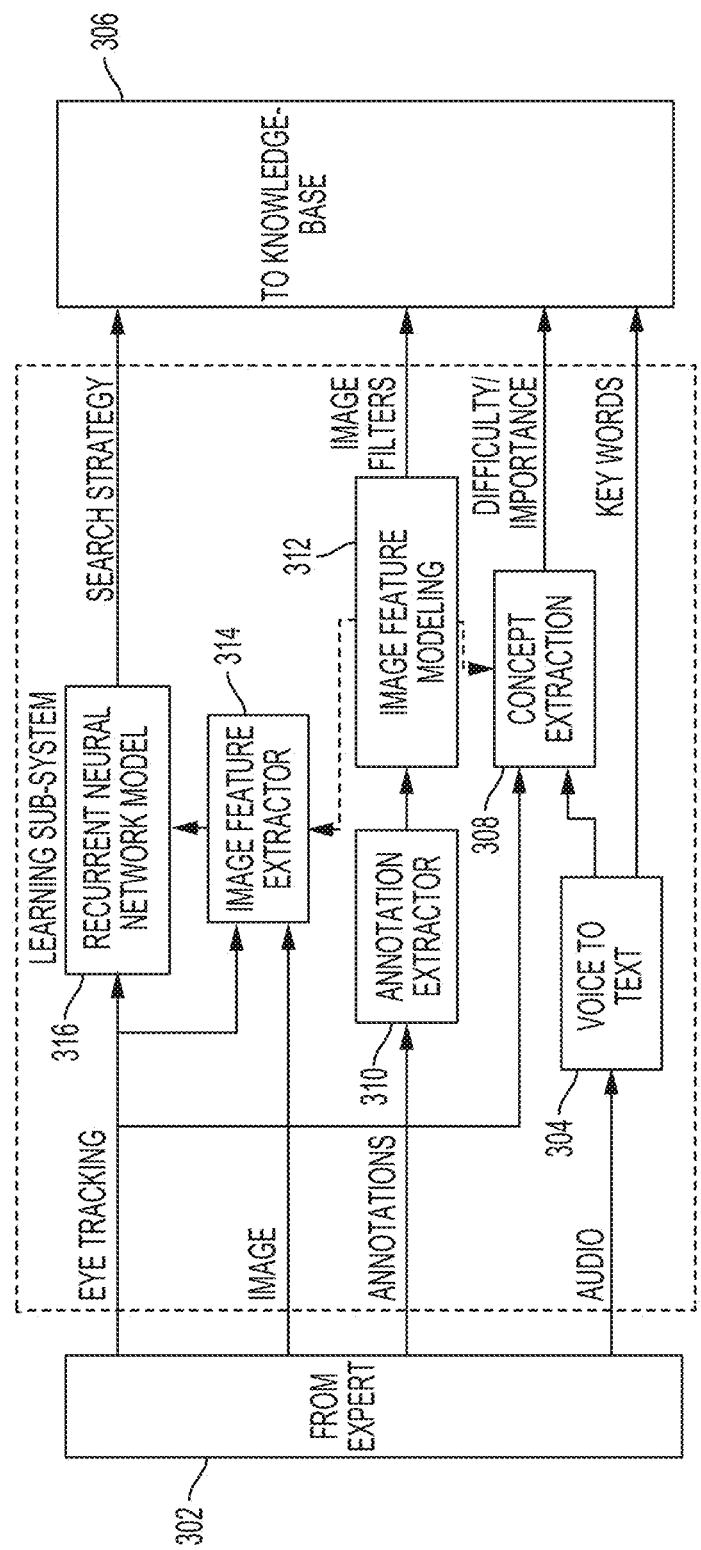
FIG. 3 is a diagram illustrating a learning module in one embodiment of the present disclosure.

FIG. 3 is a diagram illustrating a learning system in one embodiment of the present disclosure. The learning system receives inputs from different sources: eye tracking data, audio cues and image annotations. The learning system also receives image data, for example, from a knowledgebase or database of images. The different sources of data are received as a user or expert 302 inputs information while analyzing a presented image, for example, as described above with reference to FIG. 2. For example, eye tracking data is received from an eye tracking system that monitors the user's eye movement patterns on the image. Audio cues are received via a microphone to which the user may speak about the image the user is analyzing. Annotations are received via a UI receiving input signals from an input device by which the user may annotate the image on a display screen or device. Image data is received from a database of images. Voice to text component 304 translates the received audio data into text. Keywords are extracted from the translated text and saved in a knowledge base 206.

A concept extraction component 308 may receive the translated text from the voice to text component 304 and also the eye tracking data. For example, the concept extraction module 308 takes three messages (signals) as input: eye-tracking data, image features corresponding to an annotation and keyword text (keywords uttered by expert converted to text). This module 308 then attaches a difficulty and/or importance label (e.g., difficult to identify pathology in region, easy to identify pathology in region, region highly important for the diagnosis of the image, region of medium importance for image diagnosis, region of low importance for image diagnosis) to the image regions. The difficulty label (e.g., difficult to identify pathology in region, easy to identify pathology in region) is derived using the time spent on a region (e.g., difficult if the time spent on the region is greater than a specific threshold) gained through eye tracking, and keywords (e.g., a threshold number of keywords matched against a list of known words to describe difficulty). The importance labels are derived using keywords. Once the labels are derived they are coupled with the corresponding image features from 312 and are sent to the knowledge base 306.

An annotation extractor 310 (e.g., annotation extractor 212 shown in FIG. 2) extracts annotations made by the user from image. For example, the annotation extractor 310 performs the functions described above with respect to the annotation extractor 212 shown in FIG. 2, and derives an image region that is annotated by an expert. The annotation extractor 310 learns convolutions kernel representation of the annotated regions.

Image feature modeling component 312 takes the annotations extracted by the annotation extractor 310, and trains the CNN. The CNN outputs image filters, for example, convolution kernels. The output is stored in the knowledge-base 306.

Image feature extractor 314 uses the image filters learned by the module 312 to extract features from images at locations fixated by the expert (e.g., identified through eye tracking). The extracted features are then fed in to a recurrent neural network model 316.

Recurrent neural network model 316 models eye pattern sequences. The recurrent neural network model 316 models a search sequence followed by the expert ophthalmologist so that the model can be used to show a student or the like, what the best search strategy would be for a given new image. The expert search sequence is modeled using recurrent neural network architecture. FIG. 4 is a diagram illustrating recurrent neural network architecture used in modeling the expert search sequence. In one embodiment, the model that evaluates the likelihood that a sequence would be followed by an expert is built as follows. The system extracts the features of each image region traversed by the expert in sequence (X0, X1, . . . , Xt, . . . ). These features are extracted using the convolutional neural network filters learned through image annotations. The system also extracts the next image region visited by each expert and the time spent on each region as Ri+1, Ti (from eye tracking). The system then models the likelihood function, dynamic model and the output function using neural networks with weight matrix L, D, U respectively. Once the model is designed the modeling parameters L, D, U (weights of a neural network) are learned using the back propagation technique. The learned model is then saved in the knowledgebase 306 as shown in the arrow labeled "search strategy".

Figure 5:
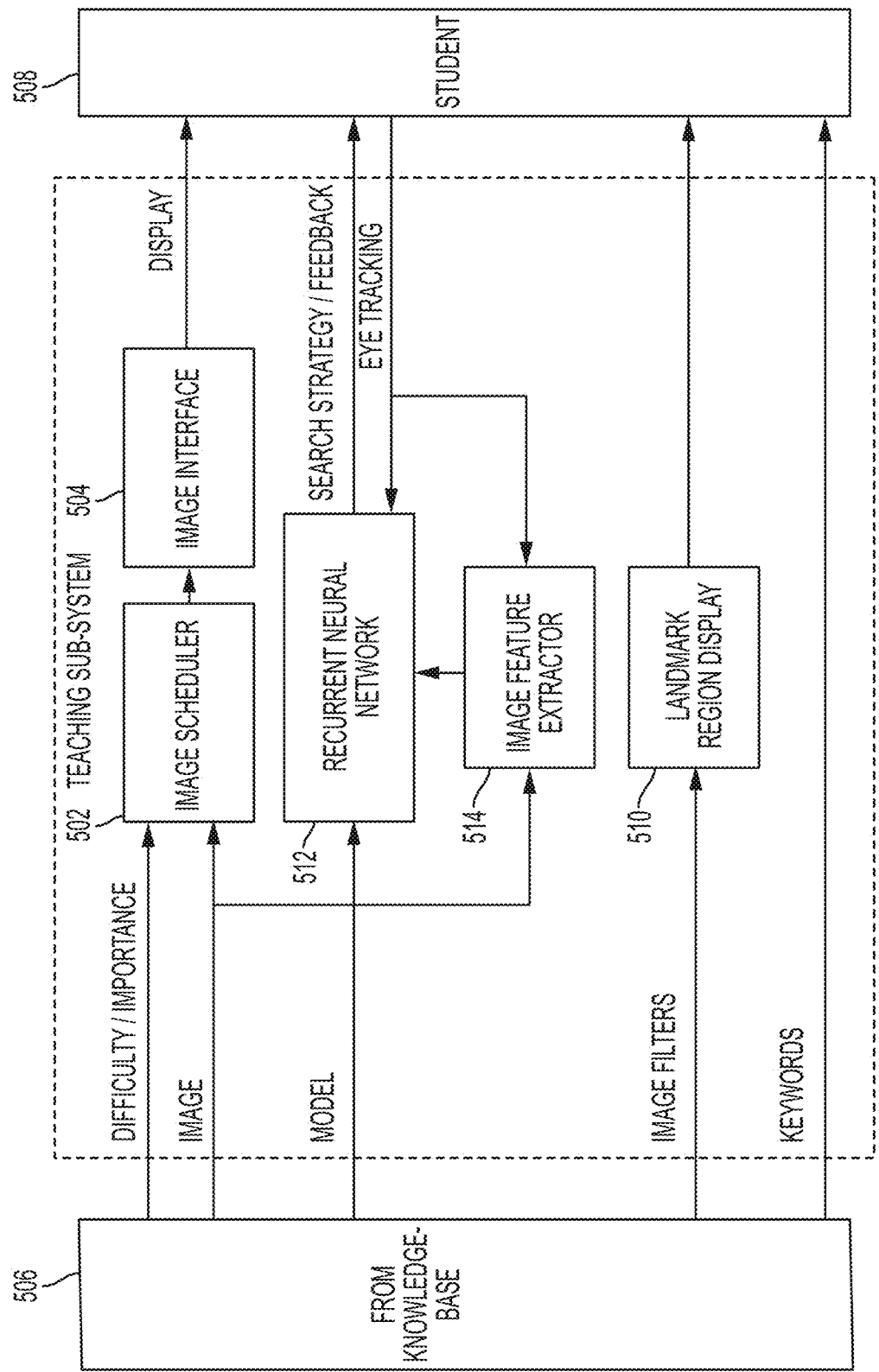
FIG. 5 is a diagram illustrating a teaching module in one embodiment of the present disclosure.

FIG. 5 is a diagram illustrating components of a teaching module or system in one embodiment of the present disclosure. The components of the teaching system execute on one or more hardware processors coupled to memory or storage, and for example, a communication network. The teaching module may present a new image selected by an image scheduler to a student and provide the student a fixed time to analyze the image. The teaching module may record the student's eye movement and also take the student through the expert analysis sequence while presenting the student with audio cues. The teaching module may provide feedback on the sequence followed by student, enable the student to explore individual pathologies and enable the student to explore similar and complementary cases.

An image scheduler 502 selects from a knowledge base 506 (e.g., 306 at FIG. 3) an image and displays the image on a user interface (e.g., image interface) 504 to a user (e.g., a student) 508, for instance, as a visual display on a user interface (UI), e.g., graphical user interfere (GUI). The image scheduler 502 may select an image that has been made available, for example, responsive to acquiring an image scan of an object to be analyzed. For multiple scans, the image scheduler 502 selects or schedules images in the order that they are acquired, for example, the first acquired scan may be selected to be annotated first. An image identifier (ID) associated with the image, and stored knowledge base is uploaded to a teaching system's memory. The user interface 504 may prompt the user 508 to enter a pre-assigned user ID to start a new session. An eye-gaze-tracker is notified that a new session is in progress and the logic of the teaching system or UI 504 associates a reference code with the session. For instance, the logic of the teaching system or UI 504 may notify the eye-gaze-tracker. The eye-gaze tracker in one embodiment starts a new recording, e.g., eye-gaze pattern detection session identified by the reference session code. An audio recorder is also notified that a new session is in progress. The notification includes the associated reference session code. For instance, the logic of the teaching system or UI 504 may notify the audio recorder. The audio recorder starts a new audio recording session for the user. The new audio recording session is associated with or identified by the reference session code. The teaching system or the UI 504 allows the user 508 a fixed amount of time to make observations during which the eye-gaze-tracker records the user's eye movements, the audio recorder records the user's audio cues, and the UI records the user's annotations on the displayed image (image operations). It may be assumed that the user has some level of knowledge in analyzing images. The UI 504 allows the user 508 to zoom in on specific regions of the image for closer examination of the image.

For instance, a system components shown in FIG. 2 with eye-gaze tracker, a UI and audio recorder may be employed for displaying the image and receiving input from the user. For instance, an eye tracker may include at least a camera and be coupled to a hardware processor. The eye tracker may monitor eye movements of a learning user analyzing the image and a sequence of eye movements may be generated based on the eye movements monitored. The user interface, for example, may receive annotations on the image input by the learning user. A microphone may be coupled to the hardware processor, and the hardware processor may receive via the microphone audio data associated with the image spoken by the learning user. The audio data is translated into text, and keywords may be extracted from the text. The sequence of eye movements, the annotations and the keywords are correlated according to their time of occurrence. Image features from the image that are targets of the eye-gaze are extracted and mapped with the sequence of eye movements, the annotations and the keywords that are correlated.

After lapse of the fixed time, the UI 504 allows the user 508 to interact with the UI 504 to terminate and store the annotation into the system, for example, in memory or storage device. In response to the expiration of the fixed time, the eye-gaze tracker completes the session recording and the audio recorder completes the session recording. An eye-pattern-extractor extracts the relevant data points of the eye-gaze movements and time-codes them. A speech-recognition component detects and timecodes key words that have been spoken by the student.

In one embodiment, the system starts by assuming the existence of a enriched knowledge base. The image scheduler 502 shows an image via the image interface 504 to a user, e.g., a student 508. As soon as the image is displayed the eye tracker starts to track the user's (student's) eye movements. It is assumed that the user (student) has been given a task of detecting an anomaly in the image. The search strategy employed by the user (student) is recorded through the eye tracker, and the system allows the user (student) time to analyze the image.

After the system detects that the user (student) has finished visually examining the image (for example, the system detects the expiration of the time given to the user (student) to analyze the image, or for example, the user (student) inputs via the user interface an indication that the user's image analysis is completed), the image feature extractor 514 analyzes each location that the user (student) examined and extracts the features of that region. The user's eye fixation locations and their corresponding extracted features are inputted to the RNN module 512. The pre-trained model weights of RNN module 512 are loaded from the knowledge base module 506 which has the enriched database from the experts' image analysis patterns. Taking the student's initial fixation, and using the knowledge from the enriched database, the RNN module 512 predicts the search path the student should take. This predicted search path is compared with the actual search path of the student, and the corresponding error or deviation is calculated. This error quantifies how close the student's search path is to those of the experts.

The landmark region display 510 displays to the user (student) the sequence of landmarks searched by the expert, thus giving the user (student) feedback about the validity of his search strategy. The knowledge base 506 (a module that controls or interfaces to the knowledge base or data in the knowledge base) also outputs to the user (student) the sequence of keywords employed by the expert. This enhances the user's (student's) understanding of key concepts in image analysis for abnormality detection.

In one embodiment, the teaching system takes the user through the search pattern followed by a domain expert. This information is retrieved from the knowledge base 506 and displayed on a UI 504. For example, the information is searched for by looking up an identifier associated with the image in the knowledge base. The knowledge base 506 stores the identification of the displayed image and also the associated input when building the knowledge base. Part of the input includes the search strategy employed by the expert to analyze this particular image. The UI 504 automatically zooms into different parts of the image to show a focused view. For each region, the UI 504 may automatically highlight the areas that are labeled as interesting (e.g., pathologies in medical images) and provide an analysis retrieved from the knowledge base 506 to the user. In one embodiment, the information provided to the user at this stage may include: what kind of interesting features are present, how long did the expert spend on analysis, was it a difficult example, any audio cues that the expert has given on resolving ambiguities.

Once the search pattern followed by a domain expert is presented (e.g., display of expert's eye-gaze pattern, focusing or zooming in different areas of the image, any audio cues), the teaching system or the UI 504 allows the user to further explore the image. The teaching system, for example, provides an interface to closely examine interesting regions (e.g., landmark region display 510) annotated by the experts. The teaching system allows the user 508 to retrieve from a database, image examples having similar features to the first presented image. The image examples have associated knowledge base 506 constructed based on one or more domain's expert's analysis. The retrieved images may have been annotated by the same expert or different experts. In one embodiment, an expert reference ID may be used to identify various experts whose knowledge has contributed to the creation of the knowledge base 506.

The image retrieval criteria may be based on image features, key words (from audio cues), concepts (e.g., difficulty levels) or other relevant criteria. As part of the learning phase, if the user (student) is interested in examining other example images which have a similar diagnosis to the one the user (student) is currently viewing, the user (student) can retrieve these images from a database. As part of the retrieval process the user (student) supplies one or more reference criteria to search for. These criteria can be in the form of key words (e.g., audio and/or text), image features (e.g., a kind of abnormality in the image) or concepts derived from audio and/to text translator (e.g., abnormalities in a particular region or of certain severity).

Once the user (student) completes the exploration, the teaching system or UI 504 may prompt the user (student) 508 to move to the next image. The next image may be scheduled based on the user's (student's) performance. If analysis of the previous image shows that the user (student) did well then the next image that is selected is one that is progressively more challenging. The image scheduler 502 selects an image based on the strengths and weakness of a particular user, and based on the user's desire to work on aspects of a grading process. The teaching system may iterate the same process with the new image, for example, as described above, from providing a fixed time to the user to analyze the new image, recording the session, walking the user through an expert's analysis.

At the completion of a teaching session, the teaching system allows the user to achieve the following: Learn the most important landmark features and their relative importance for the task in hand; Relevant features that help in image analysis of difficult cases; Learn examples that have the potential for creating ambiguity in the learner, and how to avoid such pitfalls. While creating the enriched knowledge base the system captures the expert provided input on which images are most challenging to annotate, why it is challenging, what kind of features help in distinguishing regions that may confound a less experienced analyzer. The expert, as part of the input, may also provide and the system captures insight and/or helpful tips on how to identify the areas that are most informative and give least confusing information. Also, the feedback on specific keywords, eye tracking search strategies and image regions assist the user (student) in learning how to avoid a flawed approach to image analysis.

Figure 7:
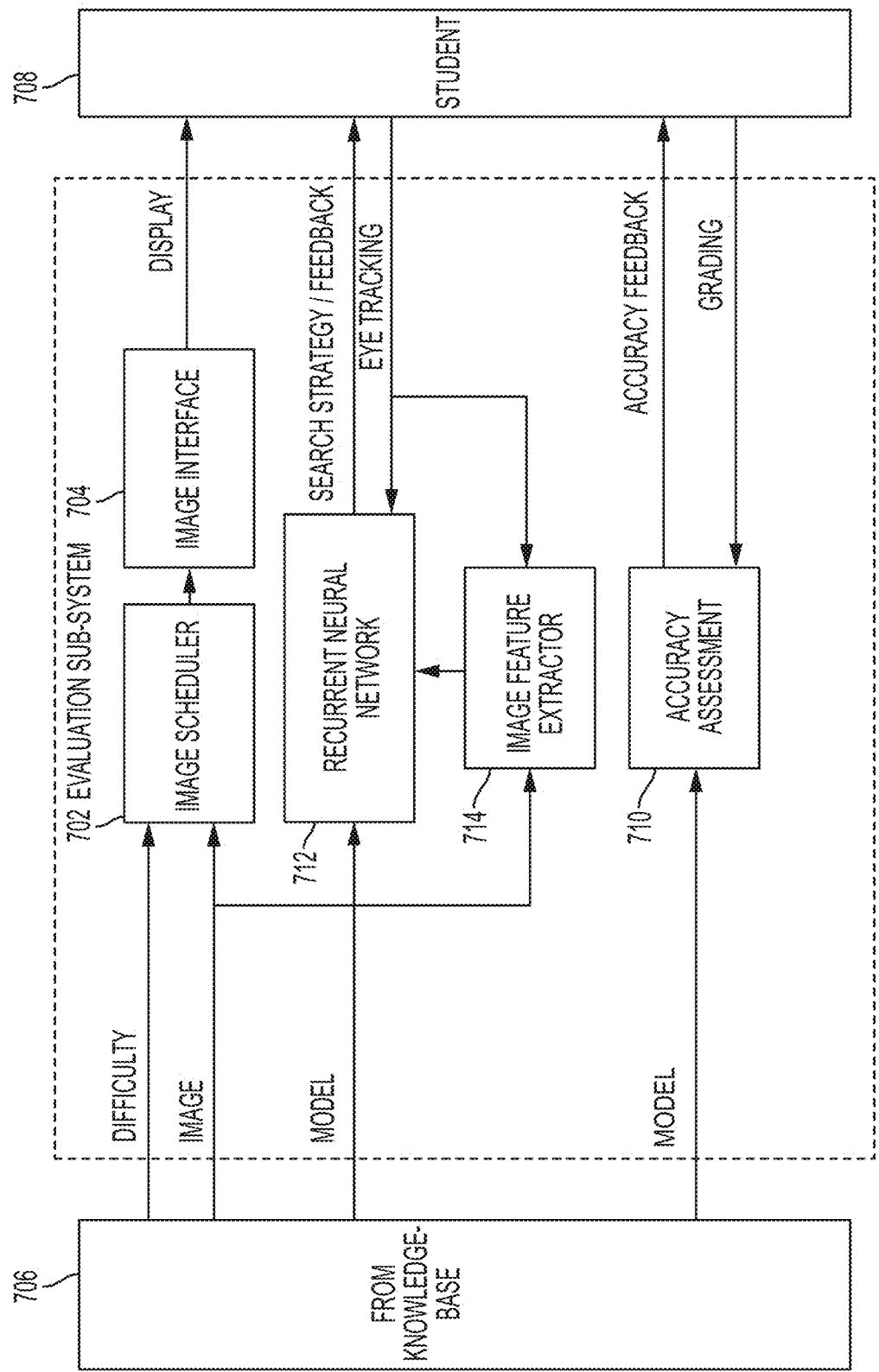
FIG. 7 is a diagram showing an evaluation module or system in one embodiment of the present disclosure.

FIG. 7 is a diagram showing an evaluation module or system in one embodiment of the present disclosure. The evaluation module in one embodiment of the present disclosure measures or evaluates a user's performance in analyzing a given image in terms of search strategy that is evaluated against a model (e.g., the search strategy built based on a domain's expert's analysis of the same image or similar image) and provides feedback on overall sequence the user followed and time spent on the analysis, for example, on each region. An image stored in the knowledge base 706 is presented through a visual display via UI 704 to the user 708. An image scheduler 702, for example, may select the image from the knowledge base 706. The associated image ID and stored knowledge base is uploaded to the evaluation system's memory. The user 708 is prompted to use a pre-assigned user ID to start a new session. The eye-gaze-tracker is notified that a new session is in progress (and a reference code is associated with the session). The eye-gaze tracker starts a new recording/eye-gaze pattern detection session identified by the reference session code. The audio recorder is notified that a new session is in progress. The notification includes the associated reference session code. The audio recorder starts a new audio recording session for the user.

The system presents a new unseen image to the user (e.g., learner), an image that has not been seen by the user (student or learner) during his learning phase. The user is asked to provide an analysis of the image within a time interval. As the user proceeds with the task of analyzing the image, the evaluation system keeps track of the user's eye movement patterns, the annotations the user makes on the image, and any audio input the user provides or speaks. The audio input is used to extract keywords and the eye tracking data is used to determine how the user fared, for example, to determine whether the user able to quickly identify the important landmarks, whether the user correctly identified all relevant landmarks, whether the user devoted adequate time in examining specific regions.

In one embodiment, the evaluation of whether the student has correctly identified all the landmarks and devoted enough time in examining specific regions is performed as follows: The eye tracking input from the device is converted into a sequence of locations and time spent. The recurrent neural network, 712, loads a model (network weights L, D, U described above) learned prior and stored in the knowledgebase. Next the image feature extractor 714 takes in the input image and the search locations from eye tracking module as input and generates a sequence of feature vectors that are fed to the recurrent neural network module. This module then presents this information to the RNN and calculates the error with respect to the current model learned from the experts. This error or the cost from the network quantifies how far the student is compared to the experts (or the model learned from the experts).

Image feature extractor 714 uses the convolutional neural network filters stored in the knowledgebase to convert the image patches to feature vectors.

Recurrent neural network 712. This module 712 models the search sequence followed by the expert ophthalmologist so that the model can be used to show a student what the best search strategy would be for a given new image.

The components 702, 704, 706, 712 and 714 may be the same components shown in FIG. 5 at 502, 504, 506, 512 and 514, providing the same functionality described with reference to FIG. 5.

Using the extracted features, the evaluation module in one embodiment provides feedback to the user on the user's performance. Specific parameters of performance measure may include: Percentage accuracy in identifying all pathological reasons; Correlation with the actual severity score as assigned by experts; User's perceived importance of different regions and/or landmarks based on his eye scanning pattern; Time taken by the user to complete the analysis. The feedback phase of the evaluation module in one embodiment uses images from the training data which has expert annotations available. The evaluation module, for example, computes different statistical parameters. For example, the following algorithm may be employed for calculating the correlation with the actual severity score as assigned by experts: the system reads the severity score (value between 0-4 for diabetic retinopathy) assigned by the expert for a test image. In case the test image is annotated by more than one expert the maximum consensus is taken as the expert severity. Then the system compares the expert severity with the severity assigned by the student. If the two matches then a score of one is given for that image and if they do not match, a score of 0 is given to that image. Ones the student finishes marking all the test images the system output the average score.

Figure 8:
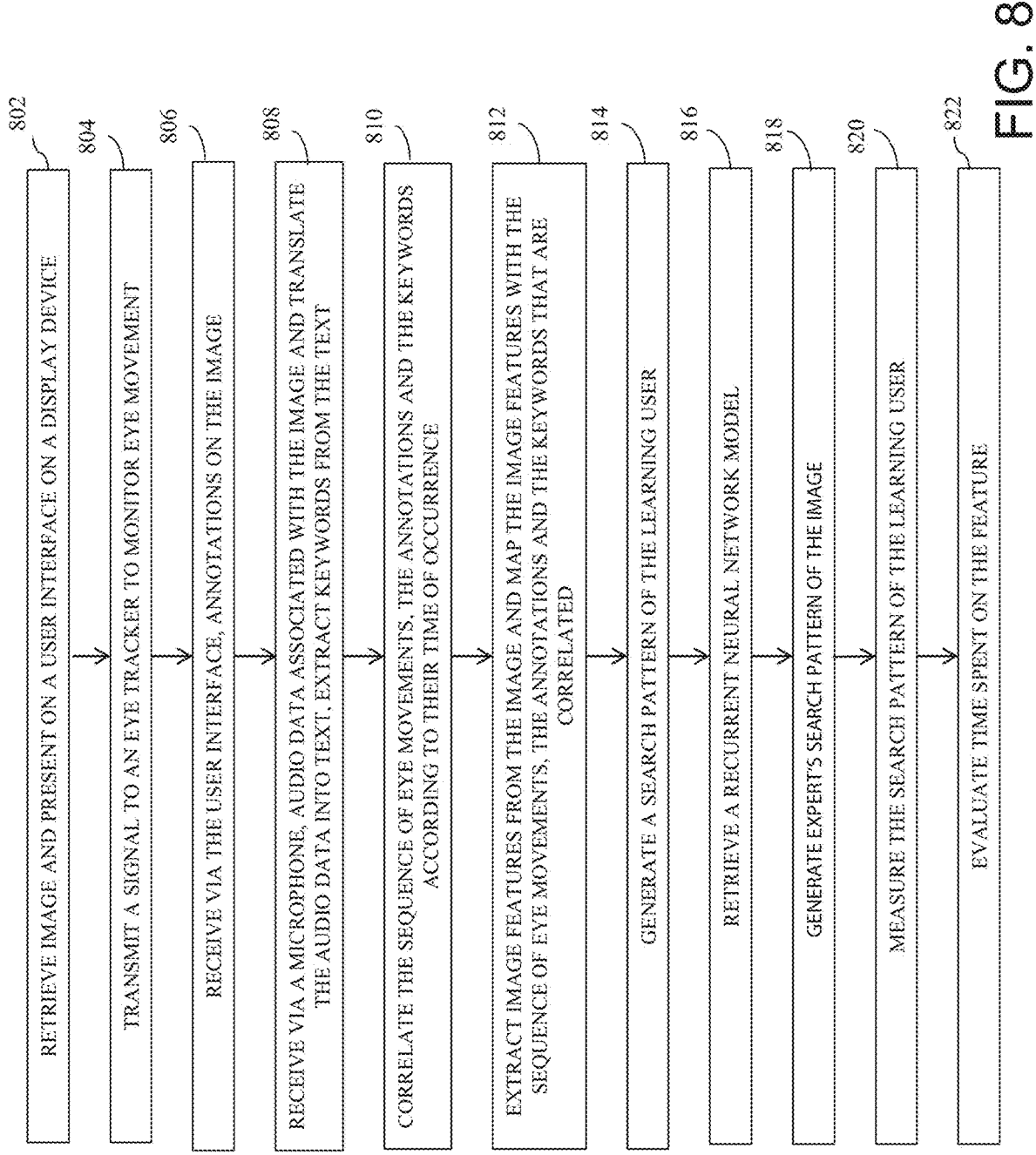
FIG. 8 is a flow diagram illustrating a method of the present disclosure in one embodiment.

FIG. 8 is a flow diagram illustrating a method of the present disclosure in one embodiment. The method may be executed by at least one hardware processor. At 802, an image from a database of images is retrieved and presented on the user interface displayed on a display device. At 804, a signal is transmitted to an eye tracker comprising at least a camera coupled to the hardware processor, the signal representing a notification to the eye tracker to monitor eye movements of a learning user analyzing the image. A sequence of eye movements is generated based on the eye tracker monitoring the eye movements. At 806, via the user interface, annotations on the image input by the learning user are received. At 808, via a microphone coupled to the hardware processor, audio data associated with the image spoken by the learning user is received. The audio data is translated into text, and keywords are extracted from the text. At 810, the method may include correlating the sequence of eye movements, the annotations and the keywords according to their time of occurrence. At 812, image features are extracted from the image and mapped with the sequence of eye movements, the annotations and the keywords that are correlated. At 814, a search pattern of the learning user is generated based on the image features mapped with the sequence of eye movements, the annotations and the keywords that are correlated. At 816, a recurrent neural network model that predicts a likelihood of an expert image analyzer focusing on a feature in the image and time spent by the expert image analyzer on the feature, are retrieved from a knowledgebase stored in a storage device. At 818, an expert's search pattern of the image is generated by executing the recurrent neural network model, and the expert's search pattern is displayed on the user interface while displaying the associated keywords retrieved from the knowledgebase. The method also may include zooming in the feature predicted by the recurrent neural network model on the user interface.

At 820, the search pattern of the learning user may be measured based on the expert's search pattern of the image. At 822, a time spent on the feature by the learning user may be evaluated against the time spent by the expert image analyzer on the feature. The learning user is provided with feedback that may include a learning user's perceived importance of different regions in the image based on the search pattern of the learning user and whether the learning user identified landmarks in the image.

Figure 9:
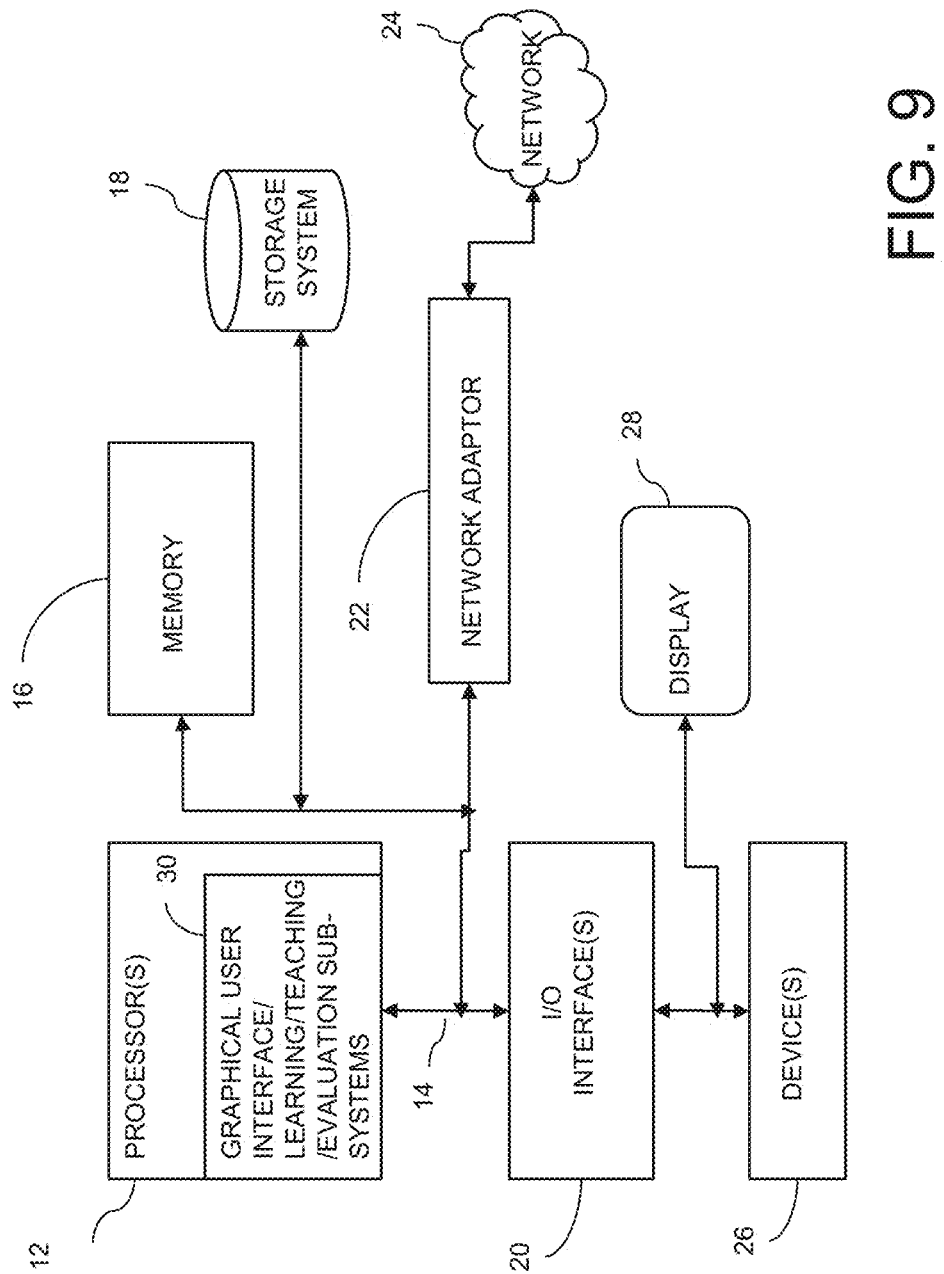
FIG. 9 illustrates a schematic of an example computer or processing system that may implement a learning, teaching and evaluation system in one embodiment of the present disclosure.

FIG. 9 illustrates a schematic of an example computer or processing system that may implement a learning, teaching and evaluation system in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 9 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module(s) 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An image analysis teaching and evaluation system, comprising:
  a hardware processor configured to execute a user interface, the hardware processor configured to retrieve an image from a database of images and cause presenting of the image on the user interface displayed on a display device;
  an eye tracker comprising at least a camera and coupled to the hardware processor, the eye tracker configured to monitor eye movements of a learning user analyzing the image and generate a sequence of eye movements;
  the user interface configured to receive annotations on the image input by the learning user;
  a microphone coupled to the hardware processor;
  the hardware processor configured to receive via the microphone audio data associated with the image spoken by the learning user, the hardware processor configured to translate the audio data into text, the hardware processor configured to extract keywords from the text;
  the hardware processor configured to correlate the sequence of eye movements, the annotations and the keywords according to their time of occurrence;
  the hardware processor configured to extract image features from the image and map the image features with the sequence of eye movements, the annotations and the keywords that are correlated;
  the hardware processor configured to generate a search pattern of the learning user based on the image features mapped with the sequence of eye movements, the annotations and the keywords that are correlated;

a knowledgebase stored in a storage device, the knowledgebase comprising a recurrent neural network model that predicts a likelihood of an expert image analyzer focusing on a feature in the image, the knowledgebase further comprising an expert image analyzer's search pattern of the image with associated audio cues and time spent by the expert image analyzer on the feature;

the hardware processor configured to generate the expert's search pattern of the image by executing the recurrent neural network model, and cause displaying of the expert's search pattern on the user interface while playing associated audio cues retrieved from the knowledgebase, the hardware processor further configured to cause zooming in the feature predicted by the recurrent neural network model on the user interface.

2. The system of claim 1, wherein the hardware processor is further configured to measure the search pattern of the learning user based on the expert's search pattern of the image.

3. The system of claim 2, wherein the hardware processor is further configured to evaluate a time spent on the feature by the learning user against the time spent by the expert image analyzer on the feature.

4. The system of claim 3, where in the hardware processor is configured to provide the learning user with feedback comprising a learning user's perceived importance of different regions in the image based on the search pattern of the learning user.

5. The system of claim 4, wherein the image comprises at least an eye image, and the feedback further comprises at least a correlation with actual severity score assigned by the expert image analyzer.

6. The system of claim 1, wherein the hardware processor is configured to allow the learning user to analyze the image and input the annotations on the image and input the audio data, for a fixed amount of time.

7. The system of claim 6, wherein the hardware processor is configured to allocate a session identifier to associate with a session comprising at least the learning user analyzing the image during the fixed amount of time.

8. A computer program product for teaching image analysis and evaluating analysis results, the computer program product comprising a computer readable storage medium having program instructions embodied therewith, wherein the computer readable storage medium is not a transitory signal per se, the program instructions readable by a processor to cause the processor to perform a method comprising: retrieving an image from a database of images and presenting the image on the user interface displayed on a display device;

transmitting a signal to an eye tracker comprising at least a camera coupled to the machine, the signal representing a notification to the eye tracker to monitor eye movements of a learning user analyzing the image and generating a sequence of eye movements based on the eye tracker monitoring the eye movements;

receiving via the user interface, annotations on the image input by the learning user;

receiving via a microphone coupled to the hardware processor, audio data associated with the image spoken by the learning user, and translating the audio data into text and extracting keywords from the text;

correlating the sequence of eye movements, the annotations and the keywords according to their time of occurrence;

extracting image features from the image and mapping the image features with the sequence of eye movements, the annotations and the keywords that are correlated;

generating a search pattern of the learning user based on the image features mapped with the sequence of eye movements, the annotations and the keywords that are correlated;

retrieving from a knowledgebase stored in a storage device, a recurrent neural network model that predicts a likelihood of an expert image analyzer focusing on a feature in the image and time spent by the expert image analyzer on the feature;

generating an expert's search pattern of the image by executing the recurrent neural network model, and displaying the expert's search pattern on the user interface while playing associated audio cues retrieved from the knowledgebase, and further zooming in the feature predicted by the recurrent neural network model on the user interface.

9. The computer program product of claim 8, further comprising measuring the search pattern of the learning user based on the expert's search pattern of the image.

10. The computer program product of claim 9, further comprising evaluating a time spent on the feature by the learning user against the time spent by the expert image analyzer on the feature.

11. The computer program product of claim 10, where in the hardware processor provides the learning user with feedback comprising a learning user's perceived importance of different regions in the image based on the search pattern of the learning user and whether the learning user identified landmarks in the image.

12. The computer program product of claim 8, wherein the learning user is allowed a fixed amount of time to analyze the image and input the annotations on the image and input the audio data.

13. The computer program product of claim 12, further comprising allocating a session identifier to associate with a session comprising the learning user analyzing the image during the fixed amount of time.

14. The system of claim 1, wherein the knowledgebase further stores a set of learned convolutional filters, which can distinguish between an identifiable normal region and an identifiable pathological region.

15. The computer program product of claim 8, wherein the knowledgebase further stores a set of learned convolutional filters, which can distinguish between an identifiable normal region and an identifiable pathological region.

* * * * *